United States Patent [19]
De Gennaro et al.

[11] Patent Number: 6,046,134
[45] Date of Patent: Apr. 4, 2000

[54] HERBICIDAL MIXTURES

[75] Inventors: Francis Patrick De Gennaro, West Des Moines, Iowa; William Francis Smith, III, Elkton, Md.

[73] Assignee: E. I. du Pont de Nemours and Company, Wilmington, Del.

[21] Appl. No.: 09/202,434

[22] PCT Filed: Jun. 18, 1997

[86] PCT No.: PCT/US97/10552

§ 371 Date: Dec. 15, 1998

§ 102(e) Date: Dec. 15, 1998

[87] PCT Pub. No.: WO97/48276

PCT Pub. Date: Dec. 24, 1997

Related U.S. Application Data

[60] Provisional application No. 60/020,197, Jun. 21, 1996.

[51] Int. Cl.[7] .............................. A01N 35/06; A01N 47/36
[52] U.S. Cl. ............................................ 504/133; 504/136
[58] Field of Search ...................................... 504/133, 136

[56] References Cited

U.S. PATENT DOCUMENTS 5,506,195  4/1996  Ensminger et al. ..................... 504/350

FOREIGN PATENT DOCUMENTS 42 16 880 A1  11/1993  Germany ........................ A01N 47/36

*Primary Examiner*—S. Mark Clardy

[57] ABSTRACT

This invention relates to herbicidal mixtures comprising 2-(4-methylsulfonyl-2-nitrobenzoyl)-1,3-cyclohexanedione in combination with one or more sulfonylureas selected from nicosulfuron, rimsulfuron, thifensulfuron methyl, primisulfuron methyl, prosulfuron, and halosulfuron methyl, herbicidal compositions of the mixtures, and a method of using the mixtures to control undesired vegetation.

10 Claims, No Drawings

HERBICIDAL MIXTURES

This application claims benefit of provisional application Ser. No. 60/020,197 filed Jun. 21, 1996.

BACKGROUND OF THE INVENTION

The control of undesired vegetation is extremely important in achieving high crop efficiency. Achievement of selective control of the growth of weeds especially in such useful crops as rice, soybeans, sugar beets, corn, potatoes, wheat, barley, tomatoes and plantation crops among others is very desirable. Unchecked weed growth in such useful crops can cause significant reduction in productivity and thereby result in increased costs to the consumers. The control of undesired vegetation in noncrop areas is also important. The need for finding products that achieve such results continues to be commercially important.

Combinations of herbicides are typically used to broaden the spectrum of plant control or enhance the level of control of any given species through additive effect. Certain rare combinations surprisingly give a greater-than-additive or synergistic effect on weeds or a less-than-additive or safening effect on the crop. The present invention relates to several such valuable combinations.

U.S. Pat. No. 5,506,196 discloses 2-[4-(methylsulfonyl)-2-nitrobenzoyl]-1,3-cyclohexanedione (named as 2-(2'-nitro-4'-methylsulfonylbenzoyl)-1,3-cyclohexanedione) and its herbicidal utility, but this reference does not disclose the herbicidal mixtures of the present invention or their surprising crop-safening effect in corn.

SUMMARY OF THE INVENTION

This invention relates to herbicidal mixtures comprising herbicidally effective amounts of the compound of Formula I and agriculturally suitable salts thereof in admixture with herbicidally effective amounts of one or more of the compounds of Formulae IIa through IIf and agriculturally suitable salts thereof. This invention also relates to herbicidal compositions comprising effective amounts of the aforesaid mixtures and at least one of the following: surfactant, solid or liquid diluent. This invention also relates to a method of controlling undesired vegetation comprising applying to the locus of the vegetation herbicidally effective amounts of the aforesaid mixtures.

The mixtures of the invention comprising the Formula I and Formulae IIa–f compounds are described below:

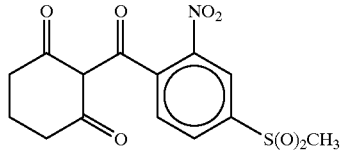

2-[4-(methylsulfonyl)-2-nitrobenzoyl]-1,3-cyclohexanedione (I);

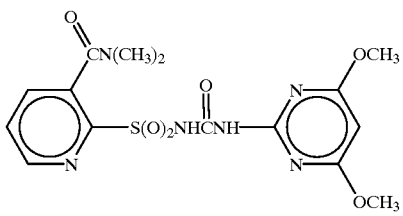

2-[[[[(4,6-dimethoxy-2-pyrimidinyl)amino]carbonyl]amnino]sulfonyl]-N,N-dimethyl-3-pyridinecarboxamide (nicosulfuron, IIa);

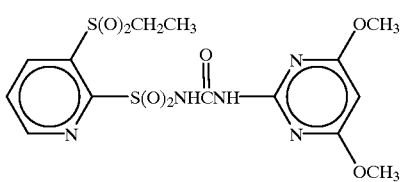

N-[[(4,6-dimethoxy-2-pyrimidinyl)amino]carbonyl]-3-(ethylsulfonyl)-2-pyridinesulfonamide (rimsulfuron, IIb);

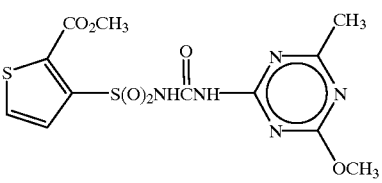

methyl 3-[[[[(4-methoxy-6-methyl-1,3,5-triazin-2-yl)amino]carbonyl]amino]sulfonyl]-2-thiophenecarboxylate (thifensulfuron methyl, IIc);

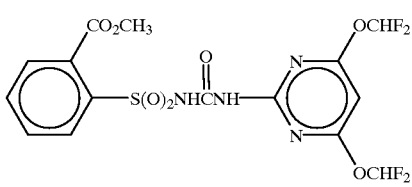

methyl 2-[[[[[4,6-bis(difluoromethoxy)-2-pyrimidinyl]amino]carbonyl]amino]sulfonyl]-benzoate (primisulfuron methyl, IId);

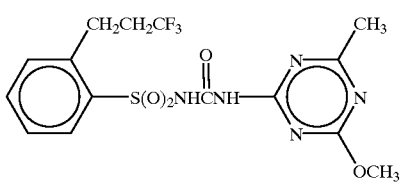

N-[[(4-methoxy-6-methyl-1,3,5-triazin-2-yl)amino]carbonyl]-2-(3,3,3-trifluoropropyl)-benzenesulfonamide (prosulfuron, IIe);

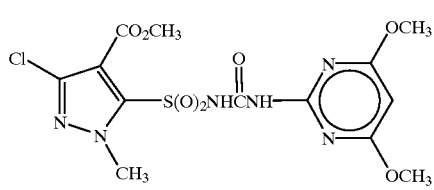
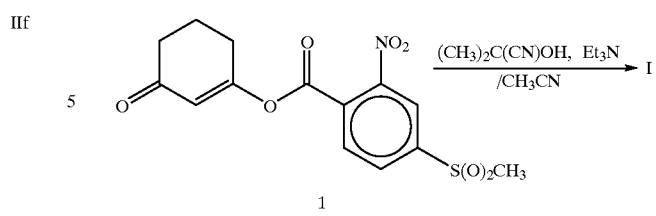

methyl 3-chloro-5-[[[[(4,6-dimethoxy-2-pyrimidinyl) amino]carbonyl]amino]sulfonyl]-1-methyl-1H-pyrazole-4-carboxylate (halosulfuron methyl, IIf).

The compounds of Formulae IIa–f and particularly the compound of Formula I can exist as one or more tautomers. One skilled in the art will recognize that said tautomers often exist in equilibrium with each other. The present invention includes mixtures of such tautomers as well as the individual tautomers of compounds of Formulae I and IIa–f.

The mixtures of the invention preferred for enhanced herbicidal utility include:

a) the compound of Formula I and the compound of Formula IIa, b) the compound of Formula I and the compound of Formula IIb, c) the compound of Formula I and the compound of Formula IIc, d) the compound of Formula I and the compound of Formula IId, e) the compound of Formula I and the compound of Formula IIe, and f) the compound of Formula I and the compound of Formula IIf.

The herbicidal compositions of the invention preferred for enhanced herbicidal utility include:

a) the compound of Formula I and the compound of Formula IIa, b) the compound of Formula I and the compound of Formula IIb, c) the compound of Formula I and the compound of Formula IIc, d) the compound of Formula I and the compound of Formula IId, e) the compound of Formula I and the compound of Formula IIe, and f) the compound of Formula I and the compound of Formula IIf, and at least one of the following: surfactant, solid or liquid diluent.

For reason of weed control spectrum and/or crop selectivity, the preferred crop for application of the mixtures of this invention is corn (maize).

DETAILS OF THE INVENTION

The benzoyl cyclohexanedione compound of Formula I can be prepared as described in U.S. Pat. No. 5,006,158. The synthesis involves rearrangement of the enol ester of Formula 1 in the presence of acetone cyanohydrin and triethylamine in acetonitrile.

Nicosulfuron (Formula IIa) is commercially available in herbicidal compositions sold by E. I. du Pont de Nemours and Company. Although nicosulfuron is most conveniently obtained as a commercial product, it can be prepared by methods described in U.S. Pat. No. 4,789,393.

Rimsulfuron (Formula IIb) is commercially available in herbicidal compositions sold by E. I. du Pont de Nemours and Company. Although rimsulfuron is most conveniently obtained as a commercial product, it can be prepared by methods described in U.S. Pat. No. 5,102,444.

Thifensulfuron methyl (Formula IIc) is commercially available in herbicidal compositions sold by E. I. du Pont de Nemours and Company. Although thifensulfuron methyl is most conveniently obtained as a commercial product, it can be prepared by methods described in U.S. Pat. No. 4,481,029.

Primisulfuron methyl (Formula IId) is commercially available in herbicidal compositions sold by Ciba-Geigy Corporation. Although primisulfuron methyl is most conveniently obtained as a commercial product, it can be prepared by methods described in U.S. Pat. No. 4,478,635.

Prosulfuron (Formula IIe) is commercially available in herbicidal compositions sold by Ciba-Geigy Corporation. Although prosulfuron is most conveniently obtained as a commercial product, it can be prepared by methods described in U.S. Pat. No. 4,671,819.

Halosulfuron methyl (Formula IIf) is commercially available in herbicidal compositions sold by the Monsanto Company. Although halosulfuron methyl is most conveniently obtained as a commercial product, it can be prepared by methods described in U.S. Pat. No. 4,668,277.

The mixtures of the present invention can include the benzoyl cyclohexanone of Formula I and the sulfonylureas of Formulae IIa–f as one or more agriculturally suitable salts. These can be prepared in a number of ways known in the art. For example, metal salts can be made by contacting a compound of Formulae I or IIa–f with a solution of an alkali or alkaline earth metal salt having a sufficiently basic anion (e.g., hydroxide, alkoxide, carbonate or hydride). Quaternary amine salts can be made by similar techniques.

Salts of a compound of Formulae I or IIa–f can also be prepared by exchange of one cation for another. Cationic exchange can be effected by direct contact of an aqueous solution of a salt of a compound of Formulae I or IIa–f (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formulae I or IIa–f (e.g., an alkali metal or quaternary amine salt) through a column packed with a cation-exchange resin containing the cation to be exchanged for that of the original salt and the desired product is eluted from the column. This method is particularly useful when the desired salt is water soluble (e.g., a potassium, sodium or calcium salt).

Formulation/Utility

The mixtures of the Formula I and Formulae IIa–f compounds can be formulated in a number of ways:

(a) the Formula I and Formulae IIa–f compounds can be formulated separately and applied separately or applied simultaneously in an appropriate weight ratio, e.g., as a tank mix; or (b) the Formula I and Formulae IIa–f compounds can be formulated together in the proper weight ratio.

Mixtures of the Formula I and Formulae IIa–f compounds will generally be used in formulation with an agriculturally suitable carrier comprising a liquid or solid diluent and/or an adjuvant wherein the formulation is consistent with the physical properties of the active ingredients, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredients can be (micro) encapsulated and further formed into a suspension or solid formulation; alternatively the entire formulation of active ingredient can be encapsulated (or "overcoated"). Encapsulation can control or delay release of the active ingredients. Sprayable formulations can be extended in suitable media and used at spray volumes from about one to several hundred liters per hectare. High-strength compositions are primarily used as intermediates for further formulation.

The formulations will typically contain effective amounts of active ingredients, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Chemically stabilized aqueous sulfonylurea or agriculturally suitable sulfonylurea salt dispersions are taught in U.S. Pat. No. 4,936,900. Solution formulations of sulfonylureas with improved chemical stability are taught in U.S. Pat. No. 4,599,412. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways.

EXAMPLE A

| High Strength Concentrate | |
| --- | --- |
| 2-[4-methylsulfonyl)-2-nitrobenzoyl]-1,3-cyclohexanedione | 49.2% |
| nicosulfuron | 49.3% |
| silica aerogel | 0.5% |
| synthetic amorphous fine silica | 1.0%. |

EXAMPLE B

| Wettable Powder | |
|---|---|
| 2-[4-methylsulfonyl)-2-nitrobenzoyl]-1,3-cyclohexanedione | 43.3% |
| rimsulfuron | 21.7% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE C

| Granule | |
|---|---|
| 2-[4-methylsulfonyl)-2-nitrobenzoyl]-1,3-cyclohexanedione | 6.7% |
| thifensulfuron methyl | 3.3% |
| attapulgite granules (low volatile matter, 0.71/0.30 mm; U.S.S. No. 25–50 sieves) | 90.0%. |

EXAMPLE D

| Aqueous Solution Suspension | |
|---|---|
| 2-[4-methylsulfonyl)-2-nitrobenzoyl]1,3-cyclohexanedione | 16.7% |
| primisulfuron methyl | 8.3% |
| hydrated attapulgite | 3.0% |
| crude calcium ligninsulfonate | 10.0% |
| sodium dihydrogen phosphate | 0.5% |
| water | 61.5%. |

EXAMPLE E

| Extruded Pellet | |
|---|---|
| 2-[4-methyisulfonyl)-2-nitrobenzoyl]-1,3-cyclohexanedione | 16.7% |
| prosulfuron | 8.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE F

| Wettable Powder | |
|---|---|
| 2-[4-methylsulfonyl)-2-nitrobenzoyl]-1,3-cyclohexanedione | 43.3% |
| halosulfuron methyl | 21.7% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE G

| Extruded Pellet | |
|---|---|
| 2-[4-methylsulfonyl)-2-nitrobenzoyl]-1,3-cyclohexanedione | 2.3% |
| nicosulfuron | 22.7% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE H

| Wettable Powder | |
|---|---|
| 2-[4-methylsulfonyl)-2-nitrobenzoyl]-1,3-cyclohexanedione | 59.1% |
| nicosulfuron | 5.9% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Utility

Mixtures of the compound of Formula I with the compounds of Formulae IIa–f are highly active postemergent herbicides, providing unexpected utility for control of selected grass and broadleaf weeds because of synergy on the weeds and/or safening on crops. Their unexpected safening to corn (maize) is particularly significant, because excellent control is retained of certain weeds that are agronomically important in this crop. Because of the safety of the mixtures of the present invention to corn (maize) and their efficacy in controlling certain weeds that commonly infest corn fields, these mixtures are particularly valued for selective weed control in corn farming. The mixtures are especially appreciated for their ability to antidote the albinism injury which can occur when the compound of Formula I is used separately.

The Formula I and Formulae IIa–f mixtures of this invention can additionally be used in combination with other commercial herbicides, insecticides or fungicides. A mixture of one or more additional herbicides with the Formula I and Formulae IIa–f mixtures of this invention may be particularly useful for weed control. In certain instances, combinations with other herbicides having similar spectrum of control but a different mode of action will be particularly advantageous for resistance management. Examples of other herbicides as mixture partners are: bromoxynil, cloransulam methyl, 2-[4,5-dihydro-4-methyl-4-(1-methylethyl)-5-oxo-1H-imidazol-2-yl]-5-(methoxymethyl)-3-pyridinecarboxylic acid, flumetsulam, imazaquin, imazethapyr, 3-oxetanyl 2-[[[[(4,6-dimethyl-2-pyrimidinyl) amino]-carbonyl]amino]sulfonyl]benzoate, and pyrithiobac sodium, and herbicides with a similar spectrum of control but a different mode of action such as, but not limited to: acetochlor, alachlor, atrazine, benazolin, bentazon, butylate, methyl [[2-chloro-4-fluoro-5-[(5,6,7,8-tetrahydro-3-oxo-1H,3H-[1,3,4]thiadiazolo[3,4-a]pyridazin-1-ylidene)amino] phenyl]thio]-acetate, clethodim, clopyralid, cyanazine, 2,4-D, 2,4-DB, dicamba, α,2-dichloro-5-[4-(difluoromethyl)-4,5-dihydro-3-methyl-5-oxo-1H-1,2,4-triazol-1-yl]-fluorobenzene-propanoate, dimethenamid, EPTC, fenoxaprop, fluazifop, fluazifop-P, fluminclorac pentyl ester, flumioxazin, fomesafen, glufosinate, glyphosate, haloxyfop, isoxaflutole, MCPA, metolachlor, metribuzin, mefluidide, pendimethalin, pyridate, quizalofop-ethyl, quizalofop-P-ethyl, sethoxydim, simazine, sulcotrione, thiafluamide, tridiphane and trifluralin.

Herbicidally effective amounts of the compounds of Formula I and Formulae IIa–f will vary depending on environmental conditions, formulation, method of application, amount and type of vegetation present, etc. The use rate ratios of Formula I to Formula IIa are in general 10:1 to 1:10, with ratios of 5:1 to 1:5 preferred for most uses. The use rate ratios of Formula I to Formula IIb are in general 20:1 to 1:6, with ratios of 10:1 to 1:4 preferred for most uses. The use rate ratios of Formula I to Formula IIc are in general 40:1 to 1:6, with ratios of 16:1 to 1:4 preferred for most uses. The use rate ratios of Formula I to Formula IId are in general 20:1 to 1:10, with ratios of 10:1 to 1:5 preferred for most uses. The use rate ratios of Formula I to Formula IIe are in general 20:1 to 1:10, with ratios of 5:1 to 1:5 preferred for most uses. The use rate ratios of Formula I to Formula IIf are in general 10:1 to 1:10, with ratios of 5:1 to 1:5 preferred for most uses. In general, the Formula I compound is applied at a rate from 5 to 280 g ai/ha, the Formula IIa compound is applied at a rate from 5 to 105 g ai/ha, the Formula IIb compound is applied at a rate from 4 to 30 g ai/ha, the Formula IIc compound is applied at a rate from 1 to 35 g ai/ha, the Formula IId compound is applied at a rate from 5 to 105 g ai/ha, the Formula IIe compound is applied at a rate from 5 to 105 g ai/ha, and the Formula IIf compound is applied at a rate from 5 to 105 g ai/ha. Preferably, the Formula I compound is applied at a rate from 17 to 140 g ai/ha, the Formula IIa compound is applied at a rate from 10 to 70 g ai/ha, the Formula IIb compound is applied at a rate from 5 to 20 g ai/ha, the Formula IIc compound is applied at a rate from 2 to 15 g ai/ha, the Formula IId compound is applied at a rate from 10 to 70 g ai/ha, the Formula IIe compound is applied at a rate from 10 to 70 g ai/ha, and the Formula IIf compound is applied at a rate from 10 to 70 g ai/ha.

One skilled in the art can readily determine application rates and ratios of the herbicide of Formula I to the herbicides of Formulae IIa–f as well as timing necessary for the desired level of weed control and crop safety.

The Formula I benzoyl cyclohexanone (Compound 1) is tested in combination with the Formulae IIa–f sulfonylureas (Compounds 2–7).

| Compound Number | Formula | Name |
| --- | --- | --- |
| 1 | I | 2-[4-(methylsulfonyl)-2-nitrobenzoyl]-1,3-cyclohexanedione |
| 2 | IIa | nicosulfuron |
| 3 | IIb | rimsulfuron |
| 4 | IIc | thifensulfuron methyl |
| 5 | IId | primisulfuron methyl |
| 6 | IIe | prosulfuron |
| 7 | IIf | halosulfuron methyl |

Compounds 1–7 are tested alone, and Compound 1 is tested individually in combination with each of Compounds 2–7 for control of weeds troublesome to corn farming. Said combinations are found to give good weed control with crop safety.

Colby's equation is used to calculate the expected additive herbicidal effect of the mixtures of Compound 1 with each of Compounds 2–7. Colby's equation (Colby, S. R. "Calculating Synergistic and Antagonistic Responses of Herbicide Combinations," *Weeds*, 15(1), pp 20–22 (1967)) calculates the expected additive effect of herbicidal mixtures, and for two active ingredients is of the form:

$$P_{a+b} = P_a + P_b - (P_a P_b / 100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Combinations of Compound 1 with Compounds 2, 3, 4, 5, 6 and 7 are found to provide unexpectedly superior utility through better control of certain weeds than expected by calculation from Colby's equation, thus demonstrating synergism, and/or less injury to corn than expected from Colby's equation, thus demonstrating crop safening.

The test results below illustrate the surprising safening on corn by mixtures of the invention while retaining excellent control of certain important agronomic weeds.

Test A Protocol

*Zea mays* (corn, maize) cultivars 'Dekalb 646' (ZEAMXA1), 'Cargill 809' (ZEAMXA2), 'Pioneer 3489' (ZEAMXA3), 'MO17 x B73' (ZEAMXA4), 'Mycogen 2759' (ZEAMXA5) and 'Pioneer 3394' (ZEAMXA6), *Xanthium pensylvanicum* (cocklebur, XANTH), *Abutilon theophrasti* (velvetleaf, ABUTH), *Chenopodium album* (lambsquarters, CHEAL), *Sida spinosa* (prickly sida, SIDSP), *Solanum americanum* (American black nightshade, SOLAM) and *Sorghum halpense* (johnsongrass, SORHA) were grown in a greenhouse to the following approximate heights and leaf stages in 10-cm square pots containing a sterilized mixture of 60% sandy loam soil and 40% Metromix 360:

| | | | Application | | |
| --- | --- | --- | --- | --- | --- |
| Species | Height (cm) | Leaf Stage | Species | Height (cm) | Leaf Stage |
| ZEAMXA1 | 14 | 3 (2 collar) | XANTH | 7 | 3 |
| ZEAMXA2 | 18 | 3 (2 collar) | ABUTH | 5 | 2 |
| ZEAMXA3 | 14 | 3 (2 collar) | CHEAL | 3 | 4 |
| ZEAMXA4 | 16 | 3 (2 collar) | SIDSP | 3 | 1 |
| ZEAMXA5 | 14 | 3 (2 collar) | SOLAM | 5 | 5 |
| ZEAMXA6 | 17 | 3 (2 collar) | SORHA | 10 | 3 |

Treatments were applied to the test species by diluting the formulated Compound 1 and the technical Compound 2 in a non-phytotoxic solvent containing a surfactant, and spraying the treatments onto the plants using a stationary laboratory circulating belt sprayer calibrated to deliver 270 L/ha through a single nozzle. Compound 1 was applied alone at 35, 70, 140 and 280 g a.i./ha, Compound 2 was applied alone at 17.5 and 35 g a.i./ha, and these compounds were also applied as combinations of these application rates. Individual treatments were replicated three times. Treatments were positioned in a greenhouse in a randomized complete block design. The greenhouse was maintained at a 29° C. average day temperature and 24° C. average night temperature, and natural light in the greenhouse was supplemented with artificial light to achieve a photoperiod of 14 hours. At 4 and 14 days after spraying, the corn plants were evaluated for albinism injury as compared to control plants that were sprayed only with non-phytotoxic solvent. Crop injury was evaluated visually using a 0 to 100% scale where 0 indicates no effect and 100 indicates complete albinism. Crop injury results are listed in Tables A-1 and A-2. Weed control was also rated at 14 days after spraying. Weed control was evaluated visually using a 0 to 100% scale where 0 indicates no effect and 100 indicates complete control. Weed control results are listed in Table A-3.

TABLE A-1*

Effect on Corn Cultivars of Compound 1 and Compound 2 as Active Ingredients Alone and in Mixture at 4 Days After Treatment

| Compound | | ZEAMXA1 | | ZEAMXA2 | | ZEAMXA3 | | ZEAMXA4 | | ZEAMXA5 | | ZEAMXA6 | |
|---|---|---|---|---|---|---|---|---|---|---|---|---|---|
| 1 | 2 | Ave. | Exp. | Ave. | Exp. | Ave. | Exp. | Ave. | Exp. | Ave. | Exp. | Ave. | Exp. |
| Alone | | | | | | | | | | | | | |
| 35 | — | 0 | — | 5 | — | 0 | — | 3 | — | 0 | — | 0 | — |
| 70 | — | 2 | — | 10 | — | 5 | — | 7 | — | 0 | — | 3 | — |
| 140 | — | 15 | — | 33 | — | 18 | — | 13 | — | 17 | — | 17 | — |
| 280 | — | 38 | — | 45 | — | 33 | — | 40 | — | 33 | — | 32 | — |
| — | 17.5 | 0 | — | 0 | — | 0 | — | 0 | — | 0 | — | 0 | — |
| — | 35 | 0 | — | 0 | — | 0 | — | 0 | — | 0 | — | 0 | — |
| Mixtures | | | | | | | | | | | | | |
| 35 | 17.5 | 0 | 0 | 2 | 5 | 0 | 0 | 0 | 3 | 0 | 0 | 0 | 0 |
| 70 | 17.5 | 0 | 2 | 2 | 10 | 0 | 5 | 2 | 7 | 0 | 0 | 0 | 3 |
| 140 | 17.5 | 0 | 15 | 10 | 33 | 3 | 17 | 0 | 18 | 0 | 13 | 0 | 17 |
| 280 | 17.5 | 12 | 38 | 25 | 45 | 5 | 33 | 8 | 40 | 15 | 33 | 13 | 32 |
| 35 | 35 | 0 | 0 | 0 | 5 | 0 | 0 | 0 | 3 | 0 | 0 | 0 | 0 |
| 70 | 35 | 0 | 2 | 0 | 10 | 0 | 5 | 0 | 7 | 0 | 0 | 0 | 3 |
| 140 | 35 | 2 | 15 | 2 | 33 | 0 | 17 | 0 | 18 | 0 | 13 | 0 | 17 |
| 280 | 35 | 10 | 38 | 28 | 45 | 8 | 33 | 15 | 40 | 12 | 33 | 12 | 32 |

*Application rates are listed for Compounds 1 and 2 in g ai/ha. Ave. is the mean result observed, reported as percent albinism. Exp. is the result expected from the Colby Equation.

TABLE A-2*

Effect on Corn Cultivars of Compound 1 and Compound 2 as Active Ingredients Alone and in Mixture at 14 Days After Treatment

| Compound | | ZEAMXA1 | | ZEAMXA2 | | ZEAMXA3 | | ZEAMXA4 | | ZEAMXA5 | | ZEAMXA6 | |
|---|---|---|---|---|---|---|---|---|---|---|---|---|---|
| 1 | 2 | Ave. | Exp. | Ave. | Exp. | Ave. | Exp. | Ave. | Exp. | Ave. | Exp. | Ave. | Exp. |
| Alone | | | | | | | | | | | | | |
| 35 | — | 0 | — | 0 | — | 0 | — | 3 | — | 0 | — | 0 | — |
| 70 | — | 0 | — | 0 | — | 0 | — | 2 | — | 0 | — | 0 | — |
| 140 | — | 2 | — | 12 | — | 12 | — | 10 | — | 3 | — | 7 | — |
| 280 | — | 12 | — | 13 | — | 18 | — | 10 | — | 10 | — | 13 | — |
| — | 17.5 | 0 | — | 0 | — | 0 | — | 0 | — | 0 | — | 0 | — |
| — | 35 | 0 | — | 0 | — | 0 | — | 0 | — | 0 | — | 0 | — |
| Mixtures | | | | | | | | | | | | | |
| 35 | 17.5 | 0 | 0 | 0 | 0 | 0 | 0 | 0 | 3 | 0 | 0 | 0 | 0 |
| 70 | 17.5 | 0 | 0 | 0 | 0 | 0 | 0 | 0 | 2 | 0 | 0 | 0 | 0 |
| 140 | 17.5 | 0 | 2 | 0 | 12 | 0 | 12 | 0 | 10 | 0 | 3 | 0 | 7 |
| 280 | 17.5 | 7 | 12 | 8 | 13 | 0 | 18 | 7 | 10 | 5 | 10 | 8 | 13 |
| 35 | 35 | 0 | 0 | 0 | 0 | 0 | 0 | 0 | 3 | 0 | 0 | 0 | 0 |
| 70 | 35 | 0 | 0 | 0 | 0 | 0 | 0 | 0 | 2 | 0 | 0 | 0 | 0 |
| 140 | 35 | 0 | 2 | 2 | 12 | 0 | 12 | 0 | 10 | 0 | 3 | 0 | 7 |
| 280 | 35 | 3 | 12 | 3 | 13 | 2 | 18 | 7 | 10 | 7 | 10 | 3 | 13 |

*Application rates are listed for Compounds 1 and 2 in g ai/ha. Ave. is the mean result observed, reported as percent albinism. Exp. is the result expected from the Colby Equation.

TABLE A-3*

Control of Weeds by Compound 1 and Compound 2 as Active Ingredients Alone and in Mixture at 14 Days After Treatment

| Compound | | XANTH | | ABUTH | | CHEAL | | SIDSP | | SOLAM | | SORHA | |
|---|---|---|---|---|---|---|---|---|---|---|---|---|---|
| 1 | 3 | Ave. | Exp. | Ave. | Exp. | Ave. | Exp. | Ave. | Exp. | Ave. | Exp. | Ave. | Exp. |
| Alone | | | | | | | | | | | | | |
| 35 | — | 100 | — | 100 | — | 100 | — | 90 | — | 100 | — | 20 | — |

TABLE A-3*-continued

Control of Weeds by Compound 1 and Compound 2 as
Active Ingredients Alone and in Mixture at 14 Days After Treatment

| Compound | | XANTH | | ABUTH | | CHEAL | | SIDSP | | SOLAM | | SORHA | |
|---|---|---|---|---|---|---|---|---|---|---|---|---|---|
| 1 | 3 | Ave. | Exp. | Ave. | Exp. | Ave. | Exp. | Ave. | Exp. | Ave. | Exp. | Ave. | Exp. |
| 70 | — | 100 | — | 100 | — | 100 | — | 100 | — | 100 | — | 23 | — |
| 140 | — | 100 | — | 100 | — | 100 | — | 100 | — | 100 | — | 40 | — |
| 280 | — | 100 | — | 100 | — | 100 | — | 100 | — | 100 | — | 67 | — |
| — | 17.5 | 17 | — | 87 | — | 100 | — | 77 | — | 77 | — | 90 | — |
| — | 35 | 47 | — | 87 | — | 100 | — | 87 | — | 80 | — | 97 | — |
| Mixtures | | | | | | | | | | | | | |
| 35 | 17.5 | 93 | 100 | 100 | 100 | 100 | 100 | 97 | 98 | 100 | 100 | 90 | 92 |
| 70 | 17.5 | 97 | 100 | 100 | 100 | 100 | 100 | 97 | 100 | 100 | 100 | 97 | 92 |
| 140 | 17.5 | 97 | 100 | 100 | 100 | 100 | 100 | 100 | 100 | 100 | 100 | 97 | 98 |
| 280 | 17.5 | 100 | 100 | 100 | 100 | 100 | 100 | 100 | 100 | 100 | 100 | 100 | 97 |
| 35 | 35 | 90 | 100 | 100 | 100 | 100 | 100 | 97 | 100 | 100 | 100 | 97 | 98 |
| 70 | 35 | 97 | 100 | 100 | 100 | 100 | 100 | 100 | 100 | 100 | 100 | 93 | 98 |
| 140 | 35 | 93 | 100 | 100 | 100 | 100 | 100 | 100 | 100 | 100 | 100 | 100 | 98 |
| 280 | 35 | 100 | 100 | 100 | 100 | 100 | 100 | 100 | 100 | 100 | 100 | 100 | 99 |

*Application rates are listed for Compounds 1 and 2 in g ai/ha. Ave. is the mean result observed, reported as percent control. Exp. is the result expected from the Colby Equation.

As can be seen from Tables A-1 and A-2, Compound 1 applied alone can cause significant albinism injury on susceptible varieties of corn. In this test, the most susceptible varieties showed some injury at application rates as low as 35 g/ha. While the injury was greatest several days after treatment, residual effects were present 14 days after treatment. Adding 17.5 g/ha of Compound 2 eliminated discernible injury 14 days after treatment of application rates as high as 140 g/ha of Compound 1. Adding 35 g/ha of Compound 2 further decreased the injury caused by 280 g/ha of Compound 1. Table A-3 shows these combinations giving very good to excellent control of cocklebur, velvetleaf, lambsquarters, prickly sida, Arnerican black nightshade and johnsongrass. Johnsongrass is a especially troublesome weed in corn. In contrast to the safening effect on corn, the retention of very good to excellent control of johnsongrass by these mixtures is not only valuable but particularly surprising, as both johnsongrass and corn are grasses.

Test B Protocol

*Zea mays* (corn, maize) cultivars 'Dekalb 646' (ZEAMXB1), 'Cargill 809' (ZEAMXB2), 'Pioneer 3489' (ZEAMXB3), 'MO17 x B73' (ZEAMXB4), 'LH192xLH221' (ZEAMXB5) and 'Pioneer 3394' (ZEAMXB6), *Xanthium pensylvanicum* (cocklebur, XANTH), *Abutilon theophrasti* (velvetleaf, ABUTH), *Chenopodium album* (lambsquarters, CHEAL), *Sida spinosa* (prickly sida, SIDSP), *Solanum ptycanthum* (eastern black nightshade) and *Sorghum halpense* (johnsongrass, SORHA) were grown in a greenhouse to the following approximate heights and leaf stages in 10-cm square pots containing a sterilized mixture of 60% sandy loam soil and 40% Metromix 360:

| Species | Height (cm) | Leaf Stage | Species | Height (cm) | Leaf Stage |
|---|---|---|---|---|---|
| | | | | Application | |
| ZEAMXB1 | 14 | 3 (2 collar) | XANTH | 8 | 3 |
| ZEAMXB2 | 19 | 3 (2 collar) | ABUTH | 6 | 3 |
| ZEAMXB3 | 13 | 3 (2 collar) | CHEAL | 3 | 6 |
| ZEAMXB4 | 10 | 2 (1 collar) | SIDSP | 3 | 2 |
| ZEAMXB5 | 12 | 3 (2 collar) | SOLPT | 2 | 3 |
| ZEAMXB6 | 18 | 3 (2 collar) | SORHA | 11 | 4 |

Treatments were applied to the test species by diluting the formulated Compound 1 and the technical Compound 3 in a non-phytotoxic solvent containing a surfactant, and spraying the treatments onto the plants using a stationary laboratory circulating belt sprayer calibrated to deliver 270 L/ha through a single nozzle. Compound 1 was applied alone at 35, 70, 140 and 280 g a.i./ha, Compound 3 was applied alone at 3 and 6 g a.i./ha, and these compounds were also applied as combinations of these application rates. Individual treatments were replicated three times. Treatments were positioned in a greenhouse in a randomized complete block design. The greenhouse was maintained at a 29° C. average day temperature and 24° C. average night temperature, and natural light in the greenhouse was supplemented with artificial light to achieve a photoperiod of 14 hours. At 4 and 14 days after spraying, the corn plants were evaluated for albinism injury as compared to control plants that were sprayed only with non-phytotoxic solvent. Crop injury was evaluated visually using a 0 to 100% scale where 0 indicates no effect and 100 indicates complete albinism. Crop injury results are listed in Tables B-1 and B-2. Weed control was also rated at 14 days after spraying. Weed control was evaluated visually using a 0 to 100% scale where 0 indicates no effect and 100 indicates complete control. Weed control results are listed in Table B-3.

TABLE B-1*

Effect on Corn Cultivars of Compound 1 and Compound 3 as
Active Ingredients Alone and in Mixture at 4 Days After Treatment

| Compound | | ZEAMXB1 | | ZEAMXB2 | | ZEAMXB3 | | ZEAMXB4 | | ZEAMXB5 | | ZEAMXB6 | |
|---|---|---|---|---|---|---|---|---|---|---|---|---|---|
| 1 | 3 | Ave. | Exp. | Ave. | Exp. | Ave. | Exp. | Ave. | Exp. | Ave. | Exp. | Ave. | Exp. |
| Alone | | | | | | | | | | | | | |
| 35 | — | 0 | — | 0 | — | 0 | — | 2 | — | 7 | — | 0 | — |
| 70 | — | 0 | — | 0 | — | 0 | — | 13 | — | 13 | — | 0 | — |
| 140 | — | 0 | — | 18 | — | 2 | — | 22 | — | 23 | — | 12 | — |
| 280 | — | 22 | — | 40 | — | 18 | — | 42 | — | 28 | — | 23 | — |
| — | 3 | 0 | — | 0 | — | 0 | — | 0 | — | 0 | — | 0 | — |
| — | 6 | 0 | — | 0 | — | 0 | — | 0 | — | 0 | — | 0 | — |
| Mixtures | | | | | | | | | | | | | |
| 35 | 3 | 0 | 0 | 0 | 0 | 0 | 0 | 0 | 2 | 0 | 7 | 0 | 0 |
| 70 | 3 | 0 | 0 | 0 | 0 | 0 | 0 | 0 | 13 | 0 | 13 | 0 | 0 |
| 140 | 3 | 0 | 0 | 0 | 18 | 0 | 2 | 0 | 22 | 0 | 23 | 0 | 12 |
| 280 | 3 | 0 | 22 | 0 | 40 | 0 | 18 | 0 | 42 | 0 | 28 | 0 | 23 |
| 35 | 6 | 0 | 0 | 3 | 0 | 0 | 0 | 0 | 2 | 0 | 7 | 0 | 0 |
| 70 | 6 | 0 | 0 | 0 | 0 | 0 | 0 | 0 | 13 | 0 | 13 | 0 | 0 |
| 140 | 6 | 0 | 0 | 0 | 18 | 0 | 2 | 0 | 22 | 0 | 23 | 0 | 12 |
| 280 | 6 | 0 | 22 | 7 | 40 | 0 | 18 | 0 | 42 | 0 | 28 | 0 | 23 |

*Application rates are listed for Compounds 1 and 3 in g ai/ha. Ave. is the mean result observed, reported as percent albinism. Exp. is the result expected from the Colby Equation.

TABLE B-2*

Effect on Corn Cultivars of Compound 1 and Compound 3 as
Active Ingredients Alone and in Mixture at 14 Days After Treatment

| Compound | | ZEAMXB1 | | ZEAMXB2 | | ZEAMXB3 | | ZEAMXB4 | | ZEAMXB5 | | ZEAMXB6 | |
|---|---|---|---|---|---|---|---|---|---|---|---|---|---|
| 1 | 3 | Ave. | Exp. | Ave. | Exp. | Ave. | Exp. | Ave. | Exp. | Ave. | Exp. | Ave. | Exp. |
| Alone | | | | | | | | | | | | | |
| 35 | — | 0 | — | 0 | — | 0 | — | 0 | — | 0 | — | 0 | — |
| 70 | — | 0 | — | 0 | — | 0 | — | 3 | — | 5 | — | 0 | — |
| 140 | — | 0 | — | 5 | — | 0 | — | 7 | — | 7 | — | 7 | — |
| 280 | — | 3 | — | 12 | — | 12 | — | 10 | — | 10 | — | 10 | — |
| — | 3 | 0 | — | 0 | — | 0 | — | 0 | — | 0 | — | 0 | — |
| — | 6 | 0 | — | 0 | — | 0 | — | 0 | — | 0 | — | 0 | — |
| Mixtures | | | | | | | | | | | | | |
| 35 | 3 | 0 | 0 | 0 | 0 | 0 | 0 | 0 | 0 | 0 | 0 | 0 | 0 |
| 70 | 3 | 0 | 0 | 0 | 0 | 0 | 0 | 0 | 3 | 0 | 5 | 0 | 0 |
| 140 | 3 | 0 | 0 | 0 | 5 | 0 | 0 | 0 | 7 | 0 | 7 | 0 | 7 |
| 280 | 3 | 0 | 3 | 0 | 12 | 0 | 12 | 0 | 10 | 0 | 10 | 0 | 10 |
| 35 | 6 | 0 | 0 | 3 | 0 | 0 | 0 | 0 | 0 | 0 | 0 | 0 | 0 |
| 70 | 6 | 0 | 0 | 0 | 0 | 0 | 0 | 0 | 3 | 0 | 5 | 0 | 0 |
| 140 | 6 | 0 | 0 | 0 | 5 | 0 | 0 | 0 | 7 | 0 | 7 | 0 | 7 |
| 280 | 6 | 0 | 3 | 7 | 12 | 0 | 12 | 0 | 10 | 0 | 10 | 0 | 10 |

*Application rates are listed for Compounds 1 and 3 in g ai/ha. Ave. is the mean result observed, reported as percent albinism. Exp. is the result expected from the Colby Equation.

TABLE B-3*

Control of Weeds by Compound 1 and Compound 3 as
Active Ingredients Alone and in Mixture at 14 Days After Treatment

| Compound | | XANTH | | ABUTH | | CHEAL | | SIDSP | | SOLAM | | SORHA | |
|---|---|---|---|---|---|---|---|---|---|---|---|---|---|
| 1 | 3 | Ave. | Exp. | Ave. | Exp. | Ave. | Exp. | Ave. | Exp. | Ave. | Exp. | Ave. | Exp. |
| Alone | | | | | | | | | | | | | |
| 35 | — | 93 | — | 100 | — | 100 | — | 73 | — | 100 | — | 19 | — |
| 70 | — | 97 | — | 100 | — | 100 | — | 83 | — | 100 | — | 20 | — |
| 140 | — | 97 | — | 100 | — | 100 | — | 87 | — | 100 | — | 30 | — |
| 280 | — | 100 | — | 100 | — | 100 | — | 93 | — | 100 | — | 40 | — |
| — | 3 | 20 | — | 100 | — | 60 | — | 43 | — | 0 | — | 90 | — |

TABLE B-3*-continued

Control of Weeds by Compound 1 and Compound 3 as
Active Ingredients Alone and in Mixture at 14 Days After Treatment

| Compound | | XANTH | | ABUTH | | CHEAL | | SIDSP | | SOLAM | | SORHA | |
|---|---|---|---|---|---|---|---|---|---|---|---|---|---|
| 1 | 3 | Ave. | Exp. | Ave. | Exp. | Ave. | Exp. | Ave. | Exp. | Ave. | Exp. | Ave. | Exp. |
| — | 6 | 77 | — | 100 | — | 73 | — | 73 | — | 0 | — | 100 | — |
| Mixtures | | | | | | | | | | | | | |
| 35 | 3 | 97 | 94 | 100 | 100 | 100 | 100 | 80 | 85 | 100 | 100 | 100 | 92 |
| 70 | 3 | 97 | 94 | 100 | 100 | 100 | 100 | 87 | 90 | 100 | 100 | 93 | 92 |
| 140 | 3 | 93 | 94 | 100 | 100 | 100 | 100 | 90 | 93 | 100 | 100 | 97 | 93 |
| 280 | 3 | 100 | 100 | 100 | 100 | 100 | 100 | 93 | 96 | 100 | 100 | 97 | 94 |
| 35 | 6 | 93 | 98 | 100 | 100 | 100 | 100 | 87 | 93 | 100 | 100 | 100 | 100 |
| 70 | 6 | 97 | 98 | 100 | 100 | 100 | 100 | 93 | 95 | 100 | 100 | 100 | 100 |
| 140 | 6 | 100 | 98 | 100 | 100 | 100 | 100 | 100 | 96 | 100 | 100 | 100 | 100 |
| 280 | 6 | 100 | 100 | 100 | 100 | 100 | 100 | 97 | 98 | 100 | 100 | 97 | 100 |

*Application rates are listed for Compounds 1 and 3 in g ai/ha. Ave. is the mean result observed, reported as percent control. Exp. is the result expected from the Colby Equation.

As can be seen from Tables B-1 and B-2, Compound 1 applied alone can cause significant albinism injury on susceptible varieties of corn. In this test, the most susceptible varities showed some injury at application rates as low as 35 g/ha. While the injury was greatest several days after treatment, residual effects were present 14 days after treatment of 70 g/ha on the most susceptible varieties. Adding 3 g/ha of Compound 3 eliminated discernible injury 14 days after treatment of application rates as high as 280 g/ha of Compound 1. Adding 6 g/ha of Compound 3 also markedly reduced injury from Compound 1. Table B-3 shows these combinations giving very good to excellent control of cocklebur, velvetleaf, lambsquarters, prickly sida, American black nightshade and johnsongrass. Johnsongrass is a especially troublesome weed in corn. In contrast to the safening effect on corn, the retention of very good to excellent control of johnsongrass by these mixtures is not only valuable but particularly surprising, as both johnsongrass and corn are grasses.

What is claimed is:

1. A herbicidally effective mixture of 2-[4-methylsulfonyl)-2-nitrobenzoyl]-1,3-cyclohexanedione and its agriculturally suitable salts with one or more herbicidal compounds selected from
    (a) nicosulfuron,
    (b) rimsulfuron,
    (c) thifensulfuron methyl,
    (d) primisulfuron methyl,
    (e) prosulfuron, and
    (f) halosulfuron methyl, and their agriculturally suitable salts.

2. The mixture of claim 1 which includes nicosulfuron.

3. The mixture of claim 1 which includes rimsulfuron.

4. The mixture of claim 1 which includes thifensulfuron methyl.

5. The mixture of claim 1 which includes primisulfuron methyl.

6. The mixture of claim 1 which includes prosulfuron.

7. The mixture of claim 1 which includes halosulfuron methyl.

8. An agriculturally suitable composition for controlling the growth of undesired vegetation comprising an effective amount of the mixture of claim 1 and at least one of the following: surfactant, solid or liquid diluent.

9. A method for controlling the growth of undesired vegetation by applying to the locus of the vegetation a herbicidally effective amount of the mixture of claim 1.

10. The method of claim 9 wherein the locus is a corn crop.

* * * * *